United States Patent [19]
de Besset

[11] Patent Number: 5,107,022
[45] Date of Patent: Apr. 21, 1992

[54] PROCESS FOR THE PREPARATION OF AROMATIC AMINES

[75] Inventor: Amaury P. de Besset, Mulhouse, France

[73] Assignee: Ciba-Geigy Corporation, Ardsley, N.Y.

[21] Appl. No.: 573,086

[22] Filed: Aug. 24, 1990

[30] Foreign Application Priority Data

Aug. 28, 1989 [CH] Switzerland ............... 3105/89

[51] Int. Cl.$^5$ .................................... C07C 233/15
[52] U.S. Cl. ........................ 564/223; 564/192; 564/215; 564/217; 564/218; 560/19; 560/43; 560/47; 558/408; 558/409
[58] Field of Search .............. 564/223, 218, 217; 558/408, 409; 560/43, 47

[56] References Cited

U.S. PATENT DOCUMENTS

| | | | |
|---|---|---|---|
| 2,407,309 | 9/1946 | Lott et al. | 260/397.7 |
| 3,891,685 | 6/1975 | Hari et al. | 260/39 |
| 4,185,036 | 1/1980 | Cossaboon | 260/580 |
| 4,283,556 | 8/1981 | Lang | 564/144 |

FOREIGN PATENT DOCUMENTS 1344796  8/1972  United Kingdom .

OTHER PUBLICATIONS

Chem. Abstract 106:34591R (1986).
Matsui et al., Chem. Abstracts 83, 96698W (1975).

*Primary Examiner*—Richard L. Raymond
*Assistant Examiner*—S. Kumar
*Attorney, Agent, or Firm*—Kevin T. Mansfield; Edward McC. Roberts

[57] ABSTRACT

The invention relates to a process for the preparation of compounds of formula

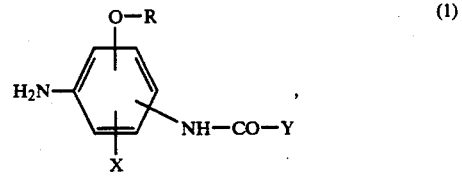

(1)

wherein R is unsubstituted or substituted $C_1$–$C_4$alkyl or unsubstituted or substituted phenyl, X is hydrogen or unsubstituted or substituted $C_1$–$C_4$alkyl, and Y is unsubstituted or substituted $C_1$–$C_4$alkyl, which process comprises subjecting compounds of formula

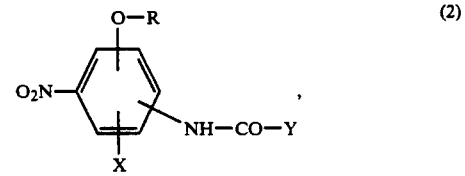

(2)

wherein R, X and Y are as defined for formula I, to catalytic hydrogenation in the alkaline pH range.

The compounds obtained by the process of this invention are suitable intermediates for the synthesis of dyes.

18 Claims, No Drawings

PROCESS FOR THE PREPARATION OF AROMATIC AMINES

The present invention relates to a novel process for the preparation of aromatic amines which contain an alkanoylamino radical and an alkoxy or phenoxy radical from the corresponding aromatic nitro compounds by catalytic hydrogenation in the alkaline pH range.

In recent years, increasing endeavours have been made to optimise processes for the manufacture of chemical compounds, especially dyes and their intermediates, both as regards the preparatory process itself as well as working up. To obtain satisfactory and reproducible results, it is necessary to rely on preparatory processes which are characterised by the following criteria: complete reaction, low proportion of by-products, simple operability of the process, ease of automation, brief sojourn times in the reactors, and the simplest possible method of working up and separation.

Numerous processes for the preparation of aromatic amines from the corresponding nitro compounds are known from the literature. Processes for the preparation of aromatic amines from the corresponding nitro compounds which contain an alkanoylamino radical and an alkoxy or phenoxy radical are not known. The disadvantage of most of these reduction and hydrogenation reactions is the unsatisfactory yield and the high proportion of by-products.

The requirement made at the present time of continuous as well as batch processes for the preparation of dyes and their intermediates is—irrespective of the quality of the starting materials—constant quality of the process products in optimum yield.

Batch processes in particular easily result in fluctuating quality of the process products induced by the varying quality of the starting materials, and the yield differs from batch to batch.

Surprisingly, the process of this invention makes it possible to prepare aromatic amines which contain an alkanoylamino and an alkoxy or phenoxy radical from the corresponding nitro compounds in simple manner and without the aforementioned shortcomings. In particular, the process of this invention substantially reduces the proportion of by-products.

Specifically, the present invention relates to a process for the preparation of compounds of formula

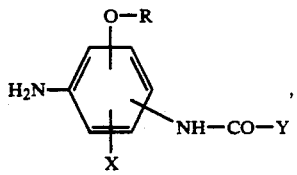

(1)

wherein R is unsubstituted or substituted $C_1-C_4$alkyl or unsubstituted or substituted phenyl, X is hydrogen or unsubstituted or substituted $C_1-C_4$alkyl, and Y is unsubstituted or substituted $C_1-C_4$alkyl, which process comprises subjecting compounds of formula

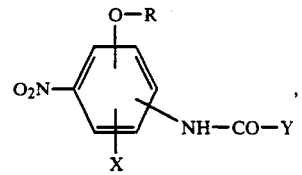

(2)

wherein R, X and Y are as defined for formula (1), to catalytic hydrogenation in the alkaline pH range.

Surprisingly, this process affords amines of formula (1) in almost quantitative yield with a very low proportion of by-products.

R, X and Y as $C_1-C_4$alkyl are, each independently of one another, conveniently: methyl, ethyl, isopropyl, n-propyl, isobutyl, n-butyl, sec-butyl and tert-butyl, which radicals may be further substituted, for example by hydroxy, halogen such as fluoro, chloro or bromo, $C_1-C_4$alkoxy such as methoxy, ethoxy, isopropoxy or n-butoxy, cyano, carboxy, carbamoyl, $C_1-C_4$alkoxycarbonyl such as methoxycarbonyl and ethoxycarbonyl, $C_1-C_4$alkylcarbonyloxy such as acetyloxy, sulfo and sulfamoyl. Illustrative of such substituted radicals R, X and Y are:

2-hydroxyethyl, 2-hydroxypropyl, 3-hydroxypropyl, 2-hydroxybutyl, 3-hydroxybutyl, 4-hydroxybutyl, 2,3-dihydroxypropyl, 2,4-dihydroxybutyl, cyanomethyl, 2-cyanoethyl, 3-cyanopropyl, methoxymethyl, ethoxymethyl, 2-methoxyethyl, 2-ethoxyethyl, 3-methoxypropyl, 3-ethoxypropyl, 2-hydroxy-3-methoxypropyl, chloromethyl, 2-chloroethyl, 2-bromoethyl, bromomethyl, 3-chloropropyl, 4-chlorobutyl, carboxymethyl, 2-carboxyethyl, 3-carboxypropyl, 4-carboxybutyl, 1,2-dicarboxyethyl, carbamoylmethyl, 2-carbamoylethyl, 3-carbamoylpropyl, methoxycarbonylmethyl, 2-methoxycarbonylethyl, 4-methoxycarbonylbutyl, 4-ethoxycarbonylbutyl, methylcarbonyloxymethyl, 3-methylcarbonyloxypropyl, 3-ethylcarbonyloxypropyl, 4-methylcarbonyloxybutyl, sulfomethyl, 2-sulfoethyl, 2-sulfopropyl, sulfamoylmethyl, 2-sulfamoylethyl.

R as phenyl is conveniently an unsubstituted or substituted phenyl radical.

Possible substituents of the phenyl radical may be: $C_1-C_4$alkyl such as methyl, ethyl, propyl, isopropyl, butyl, isobutyl, sec-butyl and tert-butyl, $C_1-C_4$alkoxy such as methoxy, ethoxy, propoxy, isopropoxy, sec-butoxy, isobutoxy and n-butoxy, halogen such as fluoro, chloro and bromo, and sulfo. Preferred substituents are methyl, ethyl, methoxy, ethoxy, chloro, bromo and sulfo.

In the process of this invention it is preferred to use compounds of formula (2), wherein the substituent R and/or the substituent X and/or the substituent Y as $C_1-C_4$alkyl is not further substituted. It is also preferred to use compounds of formula (2), wherein a phenyl radical R is not further substituted.

In a particularly preferred embodiment of the process of this invention, hydrogenation is carried out in the pH range from 7.5 to 11, most preferably from 8 to 10. The pH is made alkaline by addition of a compound which acts as a base. Ammonia or an aqueous solution of ammonia containing 20 to 40% by weight of ammonia has been found useful. In the process of this invention, the addition of the compound which acts as a base is preferably made in an amount sufficient to adjust the pH value. If ammonia is used, an amount of 4 to 40 mol %, preferably of 4 to 12 mol %, based on the molar amount of the compound of formula (2), has been found convenient.

The process of the invention is carried out in the presence of a hydrogenation catalyst. Particularly suitable hydrogenation catalysts are, typically, platinum, palladium, nickel and copper chromite catalysts. The required reaction temperature will depend essentially on the catalyst used. Reaction temperatures in the range from 30° to 250° C. have been found convenient. Preferably the reaction is carried out in the temperature range from 30° to 160° C., most preferably from 50° to 120° C., conveniently using palladium on activated charcoal as hydrogenation catalyst. The reaction can be carried out under atmospheric pressure or at an elevated pressure. If the reaction is carried out at an elevated pressure, the elevated pressure applied is normally from 0.1 to 100 bar, preferably from 1 to 30 bar. The reaction is preferably carried out at an elevated pressure.

The hydrogenation may be carried out without a solvent or in an inert solvent. Suitable solvents are, typically, alkanols (methanol, ethanol, propanol, butanol, methoxy- or ethoxyethanol), ethers (dibutyl ether, tert-butylmethyl ether, tetrahydrofuran, dioxane, ethylene glycol dimethylether, diethylene glycol dimethyl ether), amides and lactams (dimethyl formamide, dimethyl acetamide, N-methylpyrrolidone), esters and lactones (ethyl acetate, $\gamma$-butyrolactone), hydrocarbons (pentane, hexane, methylcyclohexane, benzene, toluene, xylene, chlorobenzene), and water. In the hydrogenation without the addition of a solvent, the amine formed during the hydrogenation is the solvent.

In a preferred embodiment of the process of the invention a $C_1$–$C_4$alkanol alone or in admixture with water is used as solvent. The solvent is used in the 2- to 100-fold molar amount of the compound of formula (2).

The reaction temperature is conveniently in the range from 50° to 120° C. The pressure is preferably from 1 to 30 bar. The reaction time will depend substantially on the reaction conditions and is normally less than 2 hours.

The process of this invention can be carried out by charging the nitro compound, the hydrogenation catalyst, the solvent and ammonia to an autoclave, and expelling the air first with nitrogen and then expelling the nitrogen with hydrogen. The autoclave is then closed, pressurised with hydrogen, and the contents of the autoclave are heated to the reaction temperature. Upon completion of the reaction, the catalyst is removed from the reaction mixture. The reaction product can then be stripped of the water of reaction and solvent and further purified by distillation or recrystallisation. The amines of formula (1) are known intermediates for the synthesis of dyes.

Particularly preferred embodiments of the process of this invention comprise using compounds of formula (2), wherein —X is hydrogen; —R is methyl, ethyl or phenyl, preferably methyl; and —Y is methyl or ethyl; or wherein —X is hydrogen, R is methyl and Y is methyl or ethyl.

An important embodiment of the process of the invention comprises hydrogenating compounds of formula

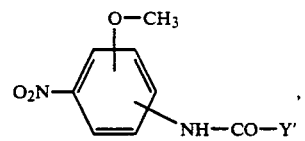

wherein Y' is methyl or ethyl, in methanol and in the presence of ammonia, at a pH of 8.5 to 10 in the presence of palladium on activated charcoal. The compound of formula (3) is preferably hydrogenated in the presence of 4 to 12 mol % of ammonia, based on the molar amount of the compound of formula (3), the hydrogenation being carried out in the presence of 0.2 to 1.0, preferably of 0.3 to 0.5, percent by weight of palladium on activated charcoal, based on the weight of the compound of formula (3).

A particularly important embodiment of the process of this invention comprises hydrogenating the compound of formula

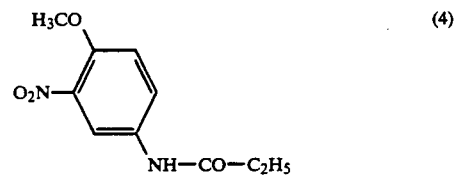

in methanol, in the presence of 4 to 12 mol % of ammonia, based on the molar amount of the compound of formula (4), and in the presence of 0.3 to 0.5 percent by weight of palladium on activated charcoal, based on the weight of the compound of formula (4), at a pressure of 15 to 25 bar, to give the compound of formula

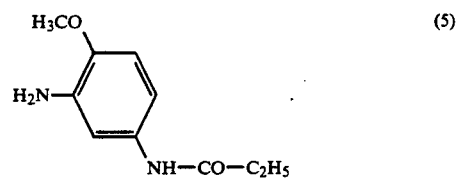

Illustrative examples of starting compounds of formula (2) are: 2-nitro-4-propionamidoanisole, 2-nitro-5-acetamidoanisole, 2-nitro-4- or -5-propionamidophenetol or 2-nitro-4- or -5-acetamidophenetol, 1-nitro-2-phenoxy-5-propionamidobenzene.

The compounds of formula (2) are known per se or they can be obtained by methods analogous to those for obtaining known compounds.

The process of this invention has the following advantages over the known processes for the preparation of the amines of formula (1):

Owing to the selective reduction/hydrogenation of the aromatic nitro compound of formula (2) in the presence of a compound which acts as a base, preferably ammonia, and in the presence of a hydrogenation catalyst, preferably palladium on activated charcoal, it is possible for the reaction to proceed more quantitatively than hitherto.

The greater purity of the compounds obtained by the process of this invention compared with the same compounds prepared in conventional manner makes it possible to obtain dyes with reproducibly improved properties.

The invention is illustrated by the following examples in which parts and percentages are by weight. Parts by weight and parts by volume stand in the same relationship to each other as the gram and the cubic centimeter.

EXAMPLE 1

114 parts of 2-nitro-4-propionamidoanisole, 160 parts of methanol, 2.5 parts of a 30% aqueous solution of ammonia and 1 part of a 50% suspension of palladium on activated charcoal, moist with water, in 2 parts of water are charged to an autoclave equipped with an aerating stirrer. The autoclave is pressurised with hydrogen and, at a pressure of 18 bar and a temperature of 80° C., hydrogenation is carried out for 1 hour. 2-Methoxy-5-propionamidoaniline is obtained in quantitative yield in a purity of >97% (analysis by liquid chromatography).

EXAMPLE 2

104 parts of 2-nitro-4-acetamidoanisole, 160 parts of ethanol, 12.5 parts of a 30% aqueous solution of ammonia and 1 part of a 50% suspension of palladium on charcoal, moist with water, in 2 parts of water are charged to an autoclave equipped with an aerating stirrer. The autoclave is pressurised with hydrogen and, at a pressure of 8 bar and a temperature of 100° C., hydrogenation is carried out for 2 hours. 2-Methoxy-5-acetamidoaniline is obtained in quantitative yield in a purity of >97% (analysis by liquid chromatography).

EXAMPLE 3

114 parts of 2-nitro-4-propionamidoanisole, 160 parts of propanol, 3.4 parts of a 30% aqueous solution of ammonia and 2 parts of a 50% suspension of palladium on activated charcoal, moist with water, in 3 parts of water are charged to an autoclave equipped with an aerating stirrer. The autoclave is pressurised with hydrogen and, at a pressure of 25 bar and a temperature of 120° C., hydrogenation is carried out for 1 hour. 2-Methoxy-5-propionamidoaniline is obtained in quantitative yield in a purity of >97% (analysis by liquid chromatography).

EXAMPLE 4

104 parts of 2-nitro-4-acetamidoanisole, 200 parts of methanol, 1.2 parts of a 30% aqueous solution of ammonia and 2 parts of a 50% suspension of palladium on charcoal, moist with water, in 2 parts of water are charged to an autoclave equipped with an aerating stirrer. The autoclave is pressurised with hydrogen and, at a pressure of 5 bar and a temperature of 100° C., hydrogenation is carried out for 2 hours. 2-Methoxy-5-acetamidoaniline is obtained in quantitative yield in a purity of >97% (analysis by liquid chromatography).

By repeating the procedure described in Examples 1 to 4 and using in place of the nitro compound in Examples 2 to 4 an equimolar amount of a nitro compound as indicated in column 2 of the following table, the amino compounds listed in column 3 of the table are obtained.

TABLE

| Example | Nitro compound | Amino compound |
|---|---|---|
| | 4-methoxy-3-nitro-acetanilide ($H_3CO$, $O_2N$, $NH-CO-CH_3$) | 4-methoxy-3-amino-acetanilide ($H_3CO$, $H_2N$, $NH-CO-CH_3$) |
| | 4-ethoxy-3-nitro-propionanilide ($H_5C_2O$, $O_2N$, $NH-CO-C_2H_5$) | 4-ethoxy-3-amino-propionanilide ($H_5C_2O$, $H_2N$, $NH-CO-C_2H_5$) |
| | 4-phenoxy-3-nitro-propionanilide ($H_5C_6O$, $O_2N$, $NH-CO-C_2H_5$) | 4-phenoxy-3-amino-propionanilide ($H_5C_6O$, $H_2N$, $NH-CO-C_2H_5$) |
| | 3-methoxy-4-nitro-propionanilide ($OCH_3$, $O_2N$, $NH-CO-C_2H_5$) | 3-methoxy-4-amino-propionanilide ($OCH_3$, $H_2N$, $NH-CO-C_2H_5$) |

TABLE-continued

| Example | Nitro compound | Amino compound |
|---|---|---|
| | 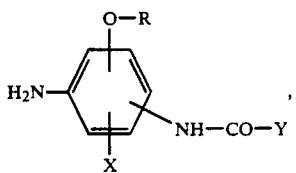 | |
| | 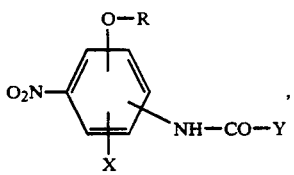 | |

What is claimed is:

1. A process for the preparation of a compound of formula $$\begin{array}{c} O-R \\ H_2N-\!\!\!\!\bigcirc\!\!\!\!-NH-CO-Y \\ X \end{array} \quad (1)$$

wherein R is $C_1$-$C_4$alkyl, unsubstituted or substituted by hydroxy, halogen, $C_1$-$C_4$alkoxy, cyano, carboxy, carbamoyl, $C_1$-$C_4$alkoxycarbonyl, $C_1$-$C_4$alkylcarbonyloxy, sulfo or sulfamoyl, or R is phenyl, unsubstituted or substituted by $C_1$-$C_4$alkyl, $C_1$-$C_4$alkoxy, halogen or sulfo, X is hydrogen or $C_1$-$C_4$alkyl unsubstituted or substituted by hydroxy, halogen, $C_1$-$C_4$alkoxy, cyano, carboxy, carbamoyl, $C_1$-$C_4$alkoxycarbonyl, $C_1$-$C_4$alkylcarbonyloxy, sulfo or sulfamoyl, and Y is $C_1$-$C_4$alkyl unsubstituted or substituted by hydroxy, halogen, $C_1$-$C_4$alkoxy, cyano, carboxy, carbamoyl, $C_1$-$C_4$alkoxycarbonyl, $C_1$-$C_4$alkylcarbonyloxy, sulfo or sulfamoyl, which process comprises subjecting compounds of formula $$\begin{array}{c} O-R \\ O_2N-\!\!\!\!\bigcirc\!\!\!\!-NH-CO-Y \\ X \end{array} \quad (2)$$

wherein R, X and Y are as defined for formula (1), to catalytic hydrogenation in the presence of a hydrogenation platinum, palladium, nickel or copper chromite catalyst in the pH range from 7.5 to 11.

2. A process according to claim 1, wherein hydrogenation is carried out in the pH range from 8 to 10.

3. A process according to claim 1, wherein hydrogenation is carried out in an inert organic solvent.

4. A process according to claim 1, wherein hydrogenation is carried out at a pressure of 0.1 to 100 bar.

5. A process according to claim 1, wherein hydrogenation is carried out at a pressure of 1 to 30 bar.

6. A process according to claim 1, wherein hydrogenation is carried out in the temperature range from 30° to 250° C.

7. A process according to claim 1, wherein hydrogenation is carried out in the temperature range from 50° to 120° C.

8. A process according to claim 1, wherein hydrogenation is carried out in the presence of palladium on activated charcoal.

9. A process according to claim 1, wherein the pH value is adjusted with ammonia or an aqueous solution of ammonia.

10. A process according to claim 1, which comprises hydrogenating a compound of formula (2), wherein X is hydrogen.

11. A process according to claim 1, which comprises hydrogenating a compound of formula (2), wherein R is methyl, ethyl or phenyl.

12. A process according to claim 11, which comprises hydrogenating a compound of formula (2), wherein R is methyl.

13. A process according to claim 1, which comprises hydrogenating a compound of formula (2), wherein Y is methyl or ethyl.

14. A process according to claim 1, which comprises hydrogenating a compound of formula

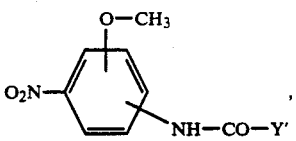

wherein Y' is methyl or ethyl, in methanol and in the presence of ammonia, at a pH of 8.5 to 10 in the presence of palladium on activated charcoal.

15. A process according to claim 14, wherein hydrogenation is carried out in the presence of 4 to 12 mol % of ammonia, based on the molar amount of the compound of formula (3).

16. A process according to claim 14, wherein hydrogenation is carried out in the presence of 0.2 to 1.0 percent by weight of palladium on activated charcoal, based on the weight of the compound of formula (3).

17. A process according to claim 14, wherein hydrogenation is carried out in the presence of 0.3 to 0.5, percent by weight of palladium on activated charcoal, based on the weight of the compound of formula (3).

18. A process according to claim 14, which comprises hydrogenating the compound of formula

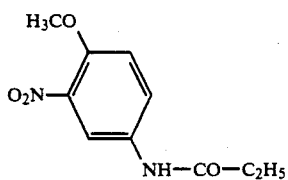
(4)
in methanol, in the presence of 4 to 12 mol % of ammonia, based on the molar amount of the compound of formula (4) and in the presence of 0.3 to 0.5 percent by weight of palladium on activated charcoal, based on the weight of the compound of formula (4), at a pressure of 15 to 25 bar, to give the compound of formula
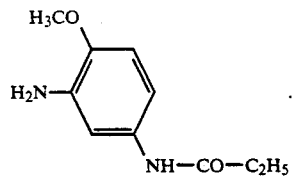
(5)
* * * * *